US010071109B2

(12) United States Patent
Elenbaas et al.

(10) Patent No.: US 10,071,109 B2
(45) Date of Patent: Sep. 11, 2018

(54) PREDICTIVE BIOMARKER FOR HYPOXIA-ACTIVATED PRODRUG THERAPY

(71) Applicant: Molecular Templates, Inc., Austin, TX (US)

(72) Inventors: Brian A. Elenbaas, Melrose, MA (US); Lei Shen, Newton, MA (US)

(73) Assignee: Molecular Templates, Inc., Austin, TX (US)

( * ) Notice: Subject to any disclaimer, the term of this patent is extended or adjusted under 35 U.S.C. 154(b) by 0 days.

(21) Appl. No.: 15/035,131

(22) PCT Filed: Oct. 28, 2014

(86) PCT No.: PCT/US2014/062532
§ 371 (c)(1),
(2) Date: May 6, 2016

(87) PCT Pub. No.: WO2015/069489
PCT Pub. Date: May 14, 2015

(65) Prior Publication Data
US 2016/0250236 A1 Sep. 1, 2016

Related U.S. Application Data

(60) Provisional application No. 61/900,821, filed on Nov. 6, 2013.

(51) Int. Cl.
*A61K 31/675* (2006.01)
*C12Q 1/6886* (2018.01)
*A61K 31/664* (2006.01)
*G01N 33/574* (2006.01)
*A61K 31/665* (2006.01)
*A61K 31/67* (2006.01)

(52) U.S. Cl.
CPC .......... *A61K 31/675* (2013.01); *A61K 31/664* (2013.01); *A61K 31/665* (2013.01); *A61K 31/67* (2013.01); *C12Q 1/6886* (2013.01); *G01N 33/57484* (2013.01); *C12Q 2600/106* (2013.01); *C12Q 2600/158* (2013.01); *G01N 2800/52* (2013.01)

(58) Field of Classification Search
CPC ........................ A61K 31/675; G01N 33/57484
See application file for complete search history.

(56) References Cited

U.S. PATENT DOCUMENTS

| | | |
|---|---|---|
| 5,472,956 A | 12/1995 | Borch et al. |
| 7,432,106 B2 | 10/2008 | Cox |
| 7,462,713 B2 | 12/2008 | Benedict et al. |
| 7,838,240 B2 | 11/2010 | Soyupak et al. |
| 8,946,275 B2 | 2/2015 | Curd et al. |
| 2003/0091574 A1 | 5/2003 | Gevas et al. |
| 2005/0232988 A1 | 10/2005 | Venkatesh et al. |
| 2006/0131994 A1 | 6/2006 | D'Angelico et al. |
| 2007/0094138 A1 | 4/2007 | Andrews |
| 2007/0117784 A1 | 5/2007 | Cleland et al. |
| 2008/0124779 A1 | 5/2008 | Oh et al. |
| 2008/0176258 A1 | 7/2008 | Pastorek et al. |
| 2009/0202989 A1 | 8/2009 | Hillan |
| 2009/0246271 A1 | 10/2009 | Wanebo |
| 2010/0048503 A1 | 2/2010 | Yamamoto |
| 2010/0137254 A1 | 6/2010 | Matteucci et al. |
| 2010/0183742 A1 | 7/2010 | Ammons et al. |
| 2010/0221754 A1 | 9/2010 | Ford et al. |
| 2010/0236340 A1 | 9/2010 | Lee et al. |
| 2011/0118230 A1 | 5/2011 | Chen et al. |
| 2011/0135739 A1 | 6/2011 | Carter et al. |
| 2011/0165562 A1 | 7/2011 | Pourahmadi et al. |
| 2011/0275088 A1 | 11/2011 | Kellner et al. |
| 2012/0089541 A1 | 4/2012 | Patel et al. |
| 2013/0102493 A1 | 4/2013 | Mueller et al. |
| 2013/0202716 A1 | 8/2013 | Curd et al. |
| 2013/0296273 A1 | 11/2013 | Curd et al. |
| 2014/0010805 A1 | 1/2014 | Hart et al. |
| 2014/0027286 A1 | 1/2014 | Ikegami et al. |
| 2014/0072624 A1 | 3/2014 | Jung et al. |
| 2014/0171389 A1 | 6/2014 | Hart et al. |
| 2015/0005262 A1 | 1/2015 | Hart et al. |
| 2015/0005263 A1 | 1/2015 | Hart et al. |
| 2015/0005264 A1 | 1/2015 | Hart |
| 2016/0296538 A1 | 10/2016 | Hart et al. |

FOREIGN PATENT DOCUMENTS

| | | |
|---|---|---|
| WO | WO-98/17810 A2 | 4/1998 |
| WO | WO-2006/035203 A1 | 4/2006 |
| WO | WO-2007/002931 A2 | 1/2007 |
| WO | WO-2008/033041 A1 | 3/2008 |
| WO | WO-2008/083101 A1 | 7/2008 |

(Continued)

OTHER PUBLICATIONS

Stenstedt et al. Anticancer Research, 2012, vol. 32, pp. 3869-3874.*
Capello et al. FEBS Letters, 2011, vol. 278, pp. 1064-1074.*
Duan, et al., "Potent and Highly Selective Hypoxia-Activated Achiral Phosphoramidate Mustards as Anticancer Drugs", J.Med Chem (51:2412-2420) (2008).
Gomez et al., "Colorectal Cancer-Specific Cytochrome P450 2W1: Intracellular Localization, Glycosylation, and Catalytic Activity," Molecular Pharmacology, vol. 78, No. 6, 2010, pp. 1004-1011.
Harlow & Lane, "Antibodies: A Laboratory Manual," 1st Edition, Cold Spring Harbor Laboratory Press, 1988.
Hoffman et al., "Evaluation of a urinary kidney biomarker panel in rat models of acute and subchronic nephrotoxicity," Toxicology, vol. 277, 2010, pp. 49-58.

(Continued)

Primary Examiner — Samira Jean-Louis
(74) Attorney, Agent, or Firm — Foley & Lardner LLP; Photon Rao

(57) ABSTRACT

CYP2W1 levels are predictive of the probability that a cancer patient will respond favorably to cancer therapy involving administration of a hypoxia-activated achiral phosphoramidate mustards.

6 Claims, 4 Drawing Sheets

(56) References Cited

FOREIGN PATENT DOCUMENTS

| WO | WO-2009/126705 A2 | 10/2009 |
|---|---|---|
| WO | WO-2009/139915 A1 | 11/2009 |
| WO | WO-2010/048330 A1 | 4/2010 |
| WO | WO-2010/081662 A2 | 7/2010 |
| WO | WO-2010/129622 | 11/2010 |
| WO | WO-2012/006032 A2 | 1/2012 |
| WO | WO-2012/008860 A2 | 1/2012 |
| WO | WO-2012/009288 A2 | 1/2012 |
| WO | WO-2012/889660 | 1/2012 |
| WO | WO-2013/116385 A1 | 8/2013 |

OTHER PUBLICATIONS

Irizarry et al., "Exploration, normalization, and summaries of high density oligonucleotide array probe level data," Biostatistics, vol. 4, No. 2, 2003, pp. 249-264.

Karlgren et al., "Tumor-specific expression of the novel cytochrome P450 enzyme," Biochemical and Biophysical Research Communications, vol. 341, 2006, pp. 451-458.

Nogrady, "Medicinal Chemistry: A Biochemical Approach", Oxford University Press, 1988, 12 pages.

Nordsmark et al., "Hypoxia in human soft tissue sarcomas: Adverse impact on survival and no association with p53 mutations," British Journal of Cancer, vol. 84, No. 8, 2001, pp. 1070-1075.

Sambrook & Russell, "Molecular Cloning: A Laboratory Manual," Cold Spring Harbor Laboratory Press, 2001.

Sun et al., "Selective Tumor Hypoxia Targeting by Hypoxia-Activated Prodrug TH-302 Inhibits Tumor Growth in Preclinical Models of Cancer," Clinical Cancer Research, vol. 18, No. 3, Feb. 2012, pp. 758-770.

"Pharmacy, 'The man and the medicament—2010'" part 3, Oral modified release formulations, 739(18), Oct. 5, 2010 [retrieved from http://apteka.ua/article/39459 on Mar. 11, 2016].

Asosingh, K. et al. (2005) "Role of the Hypoxic bone marrow microenvironment in 5T2MM murin myeloma tumor progression," The Hematology Journal 90:810-817.

Bache, M. et al. (2006) "Immunohistochemical Detection of Osteopontin in Advanced Head-and-Neck Cancer: Prognostic Role and Correlation with Oxygen Electrode Measurements, Hypoxia-Inducible-Factor-1alpha-Related Markers, and Hemoglobin Levels," Int. J. Radiation Oncology Biol. Phys. 66(5):1481-1487.

Baldo, P. et al. (2008) "mTOR pathway and mTOR inhibitors as agents for cancer therapy," Current Cancer Drug Targets 8(8):647-665.

Beasley, N.J.P. et al. (2001) "Carbonic Anhydrase IX, an Endogenous Hypoxia Marker, Expression in Head and Neck Squamous Cell Carcinoma and its Relationship to Hypoxia, Necrosis, and Microvessel Density," Cancer Research 61(13):5262-5267.

Blay, J-Y. (2010) "Updating progress in sarcoma therapy with mTOR inhibitors," Annals of Oncology:1-8.

Bortezomib (Rxlist. "Velcade" ® 2010. Available from: http://web.archive.org/web/20100124160131/http://www.rxlist.com/velcadedrug.htm.

Brenner, A. et al. (2014) "Phase 1/2 study of investigational hypoxia-targeted drug, TH-302, and bevacizumab (bev) in recurrent glioblastoma (GBM) following bev failure," 2014 ASCO, May 14. Abstract doc, http://www.thresholdpharm.com/scientific_publications.

Brenner, A. et al. (2014) "Phase 1/2 Study of Investigational Hypoxia-Targeted Drug, TH-302, and Bevacizumab in Recurrent Glioblastoma Following Bevacizumab Failure," 2014 ASCO, May 7-30. Poster doc, http://www.thresholdpharm.com/scientific_publications.

Brenner, A.J. et al. (2013) "A Dual Phase I/II Study of TH-302 and Bevacizumab in Recurrent Glioblastoma Following Bevacizumab Failure," 2013 WFNO/SNO, Nov. 21-24. Poster doc, http://www.thresholdpharm.com/scientific_publications.

Cancer [online], [retrieved on Jul. 6, 2007]. Retrieved from the Internet,URL: http://www.nlm.nih.gov/medlineplus/cancer.html.

Cavazos, D. et al. (2014) "Pharmacodynamic biomarker assessments in a phase I/II trial of the hypoxia-activated prodrug TH-302 and bevacizumab in bevacizumab-refractory recurrent glioblastoma," Neuro-Oncology 16(Suppl. 5):v60.

Chan, H-Y. et al. (2010) "Everolimus in the Treatment of Renal Cell Carcinoma and Neuroendocrine Tumors," Adv Ther. 27(8):495-511.

Chen, H. et al. (2011) "The mTOR Inhibitor Rapamycin Suppresses DNA Double-Strand Break Repair," Radiation Research 172(2):214-224.

Connell, C.M. et al. (2011) "Genomic DNA damage and ATR-Chk1 signaling determine oncolytic adenoviral efficacy in human ovarian cancer cells," The Journal of Clinical Investigation 121(4):1283-1297.

Cook, K.M. et al. (2010) "Angiogenesis Inhibitors—Current Strategies and Future Prospects," CA Cancer J Clin. 60(4):222-243.

Curd, J. et al. (2008) AACR Centennial Conference: Translational Cancer Medicine "Targeting tumor hypoxia with TH-302 and complementary chemotherapy," Clin Cancer Res. 14:AS.

Denny, W.A. (2005) "Hypoxia-activated anticancer drugs," Expert Opinion Ther. Patents. 15(6):635-646.

Dimopoulos, M. et al. (2007) "Lenalidomide plus Dexamethasone for Relapsed or Refractory Multiple Myeloma," N Engl J Med. 357:2123-2132.

Doloff, J.C. et al. (2009) "Increased Tumor Oxygenation and Drug Uptake During Anti-Angiogenic Weekly Low Dose Cyclophosphamide Enhances the Anti-Tumor Effect of Weekly Tirapazamine," Curr Cancer Drug Targets 9(6):777-788.

Dubois, L. et al. (2009) "Imaging of CA IX with fluorescent labeled sulfonamides distinguishes hypoxic and (re)-oxygenated cells in a xenograft tumour model," Radiotherapy and Oncology 92:423-428.

Dubois, L.J. et al. (2011) "Preclinical evaluation and validation of [18F]HX4, a promising hypoxia marker for PET imaging," Proc Natl Acad Sci USA 108(35):14620-14625.

Emmenegger, U. et al. (2006) "Low-dose metronomic daily cyclophosphamide and weekly Tirapazamine: A well-tolerated combination regimen with enhanced efficacy that exploits tumor hypoxia," Cancer Research 66(3):1664-16674.

Fenaux, P. et al. (2009) "Efficacy of azacitidine compared with that of conventional care regimens in the treatment of higher-risk myelodysplastic syndromes: a randomised, open-label, phase III study," Lancet Oncol. 10:223-232. (2009).

Final Office Action in U.S. Appl. No. 14/375,417, dated Sep. 20, 2016.

Fouladi, M. et al. (2007) "Phase I Study of Everolimus in Pediatric Patients With Refractory Solid Tumors," Journal of Clinical Oncology 25(30):4806-4812.

Friedman, H.S. et al. (2009) "Bevacizumab Alone and in Combination With Irinotecan in Recurrent Glioblastoma," Journal of Clinical Oncology 27(28):4733-4740.

Ganjoo, K.N. et al. (2010) "New Developments in Targeted Therapy for Soft Tissue Sarcoma," Curr Oncol. Rep. 12:261-265.

Golub, T.R. et al. (1999) "Molecular Classification of Cancer: Class Discovery and Class Prediction by Gene Expression Monitoring," Science 286:531-537.

Hart, C.P. et al. (2010) "Antiangiogenic-induced increase in tumor hypoxia in RCC and NSCLC human tumor xenografts and its selective targeting by the hypoxia-activated prodrug TH-302: A model for clinical exploration?" American Association for Cancer Research (AACR) Translational Cancer Medicine Meeting, Jul. 2010. PDF doc. http://www.thresholdpharm.com/scientific_publications.

Hu, J. et al. (2010) "Targeting the multiple myeloma hypoxic niche with TH-302, a hypoxia-activated prodrug," Blood 116(9):1524-1527.

Ivanov, S. et al. (2001) "Expression of Hypoxia-Inducible Cell-Surface Transmembrane Carbonic Anhydrases in Human Cancer," American Journal of Pathology 158(3):905-919.

Jacob, S. et al. (2001) "The role of DNA mismatch repair system in the cytotoxicity of the topoisomerase inhibitors campothecin and etoposide to human colorectal cancer cells," Cancer Res. 61(17):6555-6562, abstract, PubMed.

Jung, D. et al. (2008) "Plasma pharmacokinetics, oral bioavailability, and interspecies scaling of the hypoxically activated

(56) References Cited

OTHER PUBLICATIONS prodrug, TH-302, in mice, rat, dogs and monkeys," 99th AACR Annual Meeting mOTR/Akt/PI3K Inhibitors and Vascular/Hypoxia Targeting Agents: Poster Presentations-Proffered Abstracts.
Kharkevich, D.A. (1987) Pharmacology, Moscow, Medicina:47-48.
Kirkpatrick, J.P. et al. (2008) "Elevated CAIX Expression is Associated with an Increased Risk of Distant Failure in Early-Stage Cervical Cancer," Biomarker Insights 3:45-55.
Konopleva, M. et al. (2009) "Therapeutic targeting of microenvironmental interactions in leukemia: mechanisms and approaches," Drug Resist Updat. 12(0):103-113.
Kumar, S. et al. (2012) "Preclinical Evaluation of Antitumor Efficacy of the Hypoxia-Activated Prodrug TH-302 and Sunitinib in Neuroblastoma Mouse Models," Advances in Neuroblastoma Research (ANR) Conference, Jun. 2012. PDF doc. http://www.thresholdpharm.com/scientific_publications.
Lala, P.K. et al. (1998) "Role of nitric oxide in tumor progression: Lessons from experimental tumors," Cancer and Metastasis Reviews 17:91-106.
Li, G. et al. (2008) "Serum Carbonic Anhydrase 9 Level is Associated With Postoperative Recurrence of Conventional Renal Cell Cancer," The Journal of Urology 180:510-514.
Lu, Q. et al. (2012) "TH-302, a hypoxia-activated prodrug with broad in vivo preclinical combination therapy efficacy: optimization of dosing regimens and schedules," Cancer Chemother Pharmacol. 69(6):1487-1498.
Lynch, T.J. et al. (2009) "A Randomized Phase 2 Study of Erlotinib Alone and in Combination with Bortezomib in Previously Treated Advanced Non-small Cell Lung Cancer," J Thorac Oncol. 4(8):1002-1009.
Manegold, C. et al. (1996) "Oral ifosfamide/mesna versus intravenous ifosfamide/mesna in non-small-cell lung cancer: A randomized phase II trial of the EORTC lung cancer cooperative group," Annals of Oncology 7:637-639.
Meadows, K. et al. (2013) "Phase I Study of Pazopanib in Combination with the Investigational Hypoxia-targeted Drug TH-302," AACR-NCI-EORTC International Conference on Molecular Targets and Cancer Therapeutics, Oct. 19-23, Poster #514. Poster doc. http://www.thresholdpharm.com/scientific_publications.
Meng, F. et al. (2011) "Molecular and Cellular Pharmacology of the Hypoxia-Activated Prodrug TH-302," Mol Cancer Ther. 11(3):740-751.
Min, C-K. et al. (2007) "Bortezomib in Combination with Conventional Chemotherapeutic Agents for Multiple Myeloma Compared with Bortezomib Alone," Jpn J Clin Oncol. 37(12):961-968.
Morgan, G.J. et al. (2007) "Lenalidomide (Revlimid), in combination with cyclophosphamide and dexamethasone (RCD), in an effective and tolerated regimen for myeloma patients," British Journal of Haematology 137:268-269.
Non-Final Office Action in U.S. Appl. No. 14/375,417, dated Apr. 18, 2016.
Non-Final Office Action in U.S. Appl. No. 14/783,776, dated Mar. 24, 2017.
Papadopoulos, K.P. et al. (2008) "A Phase 1 Open-Label, Accelerated Dose-Escalation Study of the Hypoxia-Activated Prodrug AQ4N in Patients with Advanced Malignancies," Clin Cancer Res. 14(21):7110-7115.
Patterson, L.H. et al. (2000) "AQ4N: a new approach to hypoxia-activated cancer chemotherapy," British Journal of Cancer 83(12):1589-1593.
Pytel, D. et al. (2009) "Tyrosine kinase blockers: new hope for successful cancer therapy," Anticancer Agents Med Chem. 9(1):66-76, abstract, PubMed.
Reeder, C.B. et al. (2009) "Cyclophosphamide bortezomib and dexamethasone induction for newly diagnosed multiple myeloma: high response rates in a phase II clinical trial," Leukemia 23:1337-1341.
Russell, J. et al. (2009) "Immunohistochemical Detection of Changes in Tumor Hypoxia," Int J Radiation Oncology Biol Phys. 73(4):1177-1186.
Starodub, A. et al. (2013) "Phase 1 Study of TH-302, Investigational Hypoxia-Targeted Drug, in Combination with Sunitinib," AACR-NCI-EORTC International Conference on Molecular Targets and Cancer Therapeutics, Oct. 19-23, Abstract No. B77. Poster doc. http://www.thresholdpharm.com/scientific_publications.
Sun, J.D. et al. (2015) "Combination treatment with hypoxia-activated prodrug evofosfamide (TH-302) and mTOR inhibitors results in enhanced antitumor efficacy in preclinical renal cell carcinoma models," Am J Cancer Res. 5(7):2139-2155.
Tse, A.N. et al. (2007) "Targeting checkpoint kinase 1 in cancer therapeutics," Clinical Cancer Research13(7):1955-1960.
Vorinostat (National Cancer Institute. © 2009. Available from: http://web.archive.org/web/20090924062325/http://www.cancer.gov/drugdict onary/?CdrID=37944>).
Wilson, W.R. et al. (2011) "Targeting hypoxia in cancer therapy," Nature Reviews Cancer 11(6):393-410.
Wind, T.C. et al. (2011) "Measuring carbonic anhydrase IX as a hypoxia biomarker: differences in concentrations in serum and plasma using a commercial enzyme-linked immunosorbent assay due to influences of metal ions," Ann Clin Biochem 48:112-120.
Zabludoff, S.D. et al. (2008) "AZD7762 A Novel Checkpoint Kinase Inhibitor, Drives Checkpoint Abrogation and Potentiates DNA-Targeted Therapies," Mol Cancer Ther. 7(9):2955-2965.
Zaremba, T. et al. (2010) "Doxorubicin-induced suppression of poly(ADP-ribose) polymerase-1 (PARP-1) activity and expression and its implication for PARP inhibitors in clinical trials," Cancer Chemother Pharmacol. 66(4):807-812, abstract, Pubmed, retrieved [Mar. 23, 2016] from www.pubmed.com.
Zavada, J. et al. (2003) "Soluble form of carbonic anhydrase IX (CA IX) in the serum and urine of renal carcinoma patients," British Journal of Cancer 89:1067-1071.
Zuniga, Z.M. et al. (2012) "A dual phase I/II study of TH-302 and bevacizumab in resectable recurrent glioblastoma following single-agent bevacizumab failure," European Society for Medical Oncology (ESMO) 2012 Congress, Sep. 2012. PDF doc. http://www.thresholdpharm.com/scientific_publications.
Bandala, C. et al. (2012) "RNA Expression of Cytochrome P450 in Mexican Women with Cancer," Asian Pacific Journal of Cancer Prevention 13:2647-2653.
Nishida, C.R. et al. (2010) "Efficient Hypoxic Activation of the Anticancer Agent AQ4N by CYP2S1 and CYP2W1," Molecular Pharmacology 78(3):497-502.
Rubio-Viqueira, B. et al. (2007) "Optimizing the development of targeted agents in pancreatic cancer: tumor fine-needle aspiration biopsy as a platform for novel prospective ex vivo drug sensitivity assays," Molecular Cancer Therapy 6(2):515-523.
International Search Report and Written Opinion (ISA/RU) for International Application No. PCT/US2014/062532, dated Feb. 5, 2015.
Carlin, S. et al. (2012) "PET of Hypoxia: Current and Future Perspectives," J Nucl Med. 53(8):1171-1174.

* cited by examiner

PREDICTIVE BIOMARKER FOR HYPOXIA-ACTIVATED PRODRUG THERAPY

CROSS-REFERENCE TO RELATED APPLICATIONS

This application is a National Stage Application under 35 U.S.C. § 371 of International Application No. PCT/US2014/062532, filed Oct. 28, 2014, which claims priority under 35 U.S.C. § 119(e) to U.S. Provisional Application No. 61/900,821, filed Nov. 6, 2013, each of which is incorporated herein in its entirety by reference.

FIELD OF INVENTION

Provided herein are methods related to screening and/or treating cancer patients, based on their CYP2W1 level profile, with hypoxia-activated achiral phosphoramidate mustards.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment causes adverse side effects in patients and can limit the amount of anticancer drug administered to a cancer patient. It is also difficult to kill cancer cells in regions distant from the vasculature where anticancer drugs fail to penetrate.

Many cancer cells are more hypoxic relative to normal cells. Tumor hypoxia is associated with resistance to anti-cancer therapies, cancer relapse, and poor prognosis. Certain drugs in preclinical and clinical development target hypoxic cancer cells. These drugs, called hypoxia-activated prodrugs or "HAPs" are administered in an inactive, or prodrug, form but are activated, and become toxic, in a hypoxic environment. US 2010/0137254 and US 2010/0183742, each of which is incorporated herein by reference, describe HAPs such as those having a structure defined by formula (I), below:

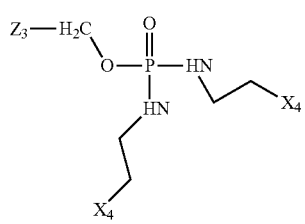

where $Z_3$ is selected from the group consisting of:

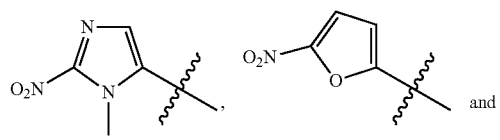

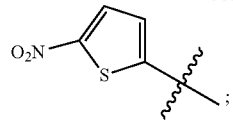

and $X_4$ is Cl or Br.

The compounds known as TH-302 and TH-281 are particularly promising therapeutic candidates. TH-302 (see Duan et al., 2008, J. Med. Chem. 51: 2412-2420, incorporated herein by reference), known by the chemical name (2-bromoethyl)({[(2-bromoethyl)amino][(2-nitro-3-methyl-imidazol-4-yl)methoxy]phosphoryl})amine, has the structure represented below:

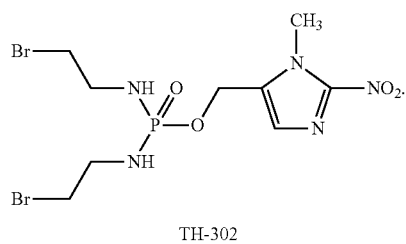

TH-302

Another promising HAP is TH-281, which differs from TH-302 only in that it has 2-chloroethyl groups instead of the 2-bromoethyl groups present in TH-302.

However, while nearly all tumors contain hypoxic regions, there is a wide variability among patients in how hypoxic a tumor of a given cancer type may be. For example, using median tumor $pO_2$ (mm Hg) as a measure of tumor hypoxia, one study of 33 soft tissue sarcoma patients showed that the median tumor pO2 ranged from about 1 to about 70 mm Hg (see Nordsmark et al., 2001, Brit. J. Cancer 84(8): 1070-1075). Another study of 58 head and neck cancer patients showed the hypoxic fraction ranged from just above 90% to 1%. Thus, if greater tumor hypoxia correlates with a better response to HAP-mediated anti-cancer therapy, then this variability in tumor hypoxia will translate into a variable response to HAP anti-cancer therapy.

"Biomarkers" generally refers to biological molecules, and quantitative and qualitative measurements of the same, that are indicative of a disease state. "Prognostic biomarkers" correlate with disease outcome, independent of therapy. For example, tumor hypoxia is a negative prognostic marker—the higher the tumor hypoxia, the higher the likelihood that the outcome of the disease will be negative. "Predictive biomarkers" indicate whether a patient is likely to respond positively to a particular therapy. For example, HER2 profiling is commonly used in breast cancer patients to determine if those patients are likely to respond to Herceptin® (trastuzumab, Genentech). "Response biomarkers" provide a measure of the response to a therapy and so provide an indication of whether a therapy is working. For example, decreasing levels of prostate specific antigen (PSA) generally indicate that anti-cancer therapy for a prostate cancer patient is working.

Hypoxia results in a number of biological responses mediated by hypoxia signal transduction pathways. Two of the primary hypoxia signal transduction pathways are the HIF (hypoxia inducible factor) pathway and the UPR (unfolded protein response) pathway. CYP2W1 (cytochrome P450, family 2, subfamily W, polypeptide 1) is an extra-hepatic cytochrome P450 enzyme that has a unique tumor-specific expression pattern (see Gomez et al., 2010, Mol. Pharmacol 78: 1004-1011; Karlgren et al., 2006, Biochem Biophys Res Comm 341: 451-458). Moreover, CYP2W1 has previously been shown to be able to reduce and activate another hypoxia-targeted prodrug called AQ4N (Nishida et al., 2010, Mol Pharmacol 78: 497-502).

There remains a need for new methods of determining whether a cancer patient is likely to respond favorably to treatment with hypoxia-activated achiral phosphoramidate mustards, such as TH-302, and/or to treat such patients. The present invention meets these needs.

SUMMARY OF THE INVENTION

The present invention arises out of the discovery that a cancer patient with high CYP2W1 level is more likely to respond favorably to HAP anti-cancer therapy than a cancer patient with a lower CYP2W1 level.

Thus, in a first aspect, the present invention provides a method for treating cancer comprising the steps of measuring CYP2W1 levels in a sample isolated from the patient, and administering a hypoxia-activated prodrug only if the CYP2W1 level measured is equal to or greater than a predetermined reference level, as may be measured, for example or without limitation, using an microarray or ELISA. In one embodiment, the CYP2W1 level is measured based on the amount of CYP2W1 RNA in the sample. Preferably, the CYP2W1 RNA level is determined relative to a control sample, e.g. as Log 2 value. More preferably, the predetermined value is 5.0 Log 2. In another embodiment, the CYP2W1 level is measured based on the amount of CYP2W1 protein in a serum sample.

In other embodiments, the sample is a plasma, serum, whole blood, or pancreatic juice sample, or a sample derived from a tumor biopsy, such as tumor lysate or tumor tissue, and the CYP2W1 level is compared to a reference CYP2W1 level of predetermined value. The reference CYP2W1 level is determined using a reference population, which may be a population of healthy individuals, or a population of cancer patients, or patient-derived xenograft (PDX) xenograft models, or any combination thereof. The reference CYP2W1 level, the level at which HAP therapy is indicated for a patient and any others with equal to or higher CYP2W1 levels, may be, for example and without limitation, the median CYP2W1 level in a reference population or some multiple of that median, such as two or three times the median CYP2W1. The predetermined value provided above were obtained using tumor samples obtained from tumor xenograft models in which CYP2W1 levels were measured using the microarray chip marketed by Affymetrix (HG_U2198 data). While similar values would be obtained using other methods and certain other sample times (blood plasma, for example), any change of sample source or CYP2W1 assay warrants additional testing to ensure that no adjustment of the predetermined value will improve results based on the different sampling or testing method employed.

The present invention involves methods that measure the expression level of CYP2W1 in the tumor by several possible methods, including RNA expression analysis (e.g., qRT-PCR, in-situ hybridization, etc.), methods of protein expression (e.g., western blotting, immunohistochemisty, FACS analysis of tumor lysates, or methods of detecting CYP2W1 protein or protein fragments in the blood). In one embodiment, the CYP2W1 levels are determined using a microarray. In other embodiments, other methods of measuring CYP2W1 levels are used. Non-limiting methods for assaying CYP2W1 include, quantitative western blots, immunohistochemistry (employing CYP2W1 antibodies) or histochemistry (employing enzyme substrates) of patient samples, including samples derived from tumor biopsies, core biopsies, and needle aspirates.

In various embodiments, the HAP administered to the patient is TH-302.

DETAILED DESCRIPTION OF THE INVENTION

Figure 1A:
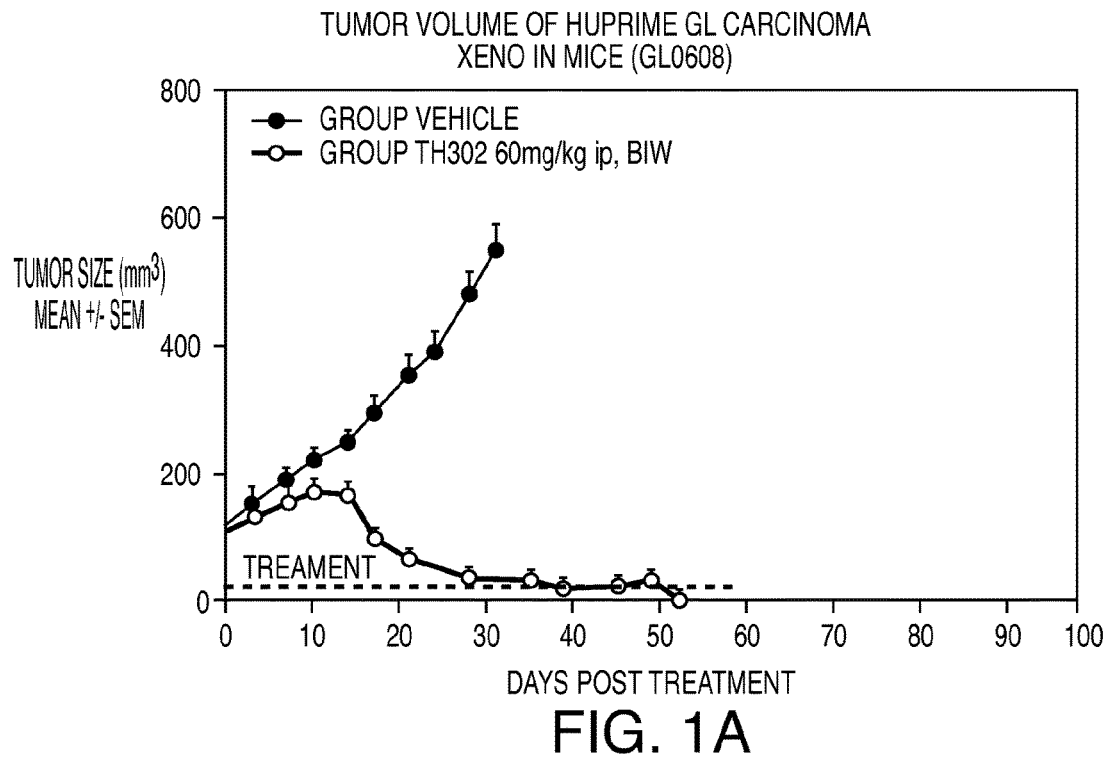
FIG. 1 shows the antitumor activity of TH-302 in 2 human gall bladder tumor PDX xenograft models (GL0608 and GL1208). In both models, TH-302 was administered at 60 mg/kg i.p. on a twice per week (Q2W) dosing schedule for the indicated dosing periods and tumor growth measurements were plotted. A: The GL0608 gall bladder cancer PDX xenograft model was highly sensitive to TH-302 with clear tumor regressions observed. The TH-302 treatment period was for 59 days. 10/10 mice had a complete response as defined by the lack of tumor re-growth following regression at day 99 which was the final tumor measurement. B: The GL1208 gall bladder cancer PDX xenograft model showed minor tumor growth inhibition (TGI) after 49 days treatment. No significant changes in the body weights of the mice treated with TH-302 were observed in these studies (data not shown).

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

"About" as used herein is used to provide flexibility to a numerical range endpoint by providing that a given value may be "a little above" or "a little below" the endpoint accounting for variations one might see in measurements taken among different instruments, samples, and sample preparations. In one aspect, "about" refers to ±20% of a quantity and includes, but is not limited to, ±15%, ±10%, and ±5% of the quantity.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Solid tumor" refers to solid tumors including, but are not limited to, metastatic tumors in bone, brain, liver, lungs, lymph node, pancreas, prostate, skin and soft tissue (sarcoma).

"Blood" refers to blood which includes all components of blood circulating in a subject including, but not limited to, red blood cells, white blood cells, plasma, clotting factors, small proteins, platelets and/or cryoprecipitate. This is typically the type of blood which is donated when a human patent gives blood. Plasma is known in the art as the yellow liquid component of blood, in which the blood cells in whole blood are typically suspended. It makes up about 55% of the total blood volume. Blood plasma can be prepared by spinning a tube of fresh blood containing an anti-coagulant in a centrifuge until the blood cells fall to the bottom of the tube. The blood plasma is then poured or drawn off. Blood plasma has a density of approximately 1025 kg/m$^3$, or 1.025 kg/l.

"Cancer" refers to leukemias, lymphomas, carcinomas, and other malignant tumors, including solid tumors, of potentially unlimited growth that can expand locally by invasion and systemically by metastasis. Examples of cancers include, but are not limited to, cancer of the adrenal gland, bone, brain, breast, bronchi, colon and/or rectum, gall bladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small cell lung tumor, non-small cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect.

"Dose" and "dosage" refer to a specific amount of active or therapeutic agents for administration. Such amounts are included in a "dosage form," which refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

"Having the same cancer" refers to comparing one patient to another or alternatively, one patient population, which may be a reference population, to another patient population. For example, the two patients or patient population will each have or be suffering from colon cancer.

"Hypoxia activated prodrug" or "HAP" refers to a prodrug wherein the prodrug is less active or inactive, relative to the corresponding drug, and comprises the drug and one or more bioreducible groups. HAPs include prodrugs that are activated by a variety of reducing agents and reducing enzymes, including without limitation single electron transferring enzymes (such as cytochrome P450 reductases) and two electron transferring (or hydride transferring) enzymes. In some embodiments, HAPs are 2-nitroimidazole triggered hypoxia-activated prodrugs. Examples of HAPs include, without limitation, TH-302 and TH-281. Methods of synthesizing TH-302 are described in US 2010/0137254 and US 2010/0183742, incorporated herein by reference.

"In-situ hybridization" is a methodology for determining the presence of or the copy number of a gene in a sample, for example, fluorescence in situ hybridization (FISH).

Generally, in-situ hybridization comprises the following major steps: (1) fixation of tissue or biological structure to be analyzed; (2) pre-hybridization treatment of the biological structure to increase accessibility of target nucleic acid, and to reduce non-specific binding; (3) hybridization of the mixture of nucleic acids to the nucleic acid in the biological structure or tissue; (4) post-hybridization washes to remove nucleic acid fragments not bound in the hybridization; and (5) detection of the hybridized nucleic acid fragments. The probes used in such applications are typically labeled, for example, with radioisotopes or fluorescent reporters. Preferred probes are sufficiently long, for example, from about 50, 100 or 200 nucleotides (nt) to about 1000 or more nucleotides, to enable specific hybridization with the target nucleic acid(s) under stringent conditions. Here, hybridization with cDNA can be accomplished, preferably by incubating at 50 to 80° C. for 10 to 20 hours, more preferably about 65° C. for 10 to 20 hours.

"Isolated" refers to molecules or biological or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

"Microarray" refers to nucleotide arrays that can be used to detect biomolecules, for instance to measure gene expression. "Array", "slide" and "(DNA) chip" are used interchangeably in this disclosure. A microarray usually comprises a basal plate, e.g. made of slide glass, silicone, or the like, and DNA fragments immobilized as an array on this basal plate. With this microarray, DNAs and/or RNAs contained in a sample can be detected by hybridizing them with the DNA fragments immobilized on the basal plate. Since the DNA and/or RNA within the sample could be radiolabeled or fluorescently labeled, detection with radio imaging scanner, fluorescence imaging scanner, or the like is possible. Various kinds of arrays are made in research and manufacturing facilities worldwide, some of which are available commercially. There are, for example, two main kinds of nucleotide arrays that differ in the manner in which the nucleic acid materials are placed onto the array substrate: spotted arrays and in-situ synthesized arrays. One of the most widely used oligonucleotide arrays is GeneChip made by Affymetrix, Inc. The oligonucleotide probes have a length of 10 to 50 nucleotides (nt), preferably 15 to 30 nt, more preferably 20 to 25 nt. They are synthesized in-silico on the array substrate. These arrays tend to achieve high densities, e.g. more than 40,000 genes per $cm^2$. The spotted arrays, on the other hand, tend to have lower densities, but the probes, typically partial cDNA molecules, usually are much longer than 25 nucleotides. A representative type of spotted cDNA array is LifeArray made by Incyte Genomics. Pre-synthesized and amplified cDNA sequences are attached to the substrate of these kinds of arrays.

"Pancreatic juice sample" refers to pancreatic secretions and isolates of such secretions obtained by a physician.

"Patient" and "subject" are used interchangeably to refer to a mammal in need of treatment for cancer or other hyperproliferative disease. Generally, the patient is a human. Generally, the patient is a human diagnosed with cancer. In certain embodiments a "patient" or "subject" may refer to a non-human mammal such as a non-human primate, a dog, cat, rabbit, pig, mouse or rat such as animals used in screening, characterizing, and evaluating drugs and therapies.

"Physiologically acceptable salt" refers to an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body. While the said compounds according to the invention can be used in their final non-salt form, the present invention also encompasses the use of these compounds in the form of their pharmaceutically acceptable salts, which can be derived from various organic and inorganic acids and bases by procedures known in the art.

"Polymerase Chain Reaction" or "PCR" is an amplification-based assay used to measure the copy number of the gene. In such assays, the corresponding nucleic acid sequences act as a template in an amplification reaction. In a quantitative amplification, the amount of amplification product will be proportional to the amount of template in the original sample. Comparison to appropriate controls provides a measure of the copy number of the gene, corresponding to the specific probe used, according to the principle known in the art.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art.

A "predetermined value" for CYP2W1 as used herein, is so chosen that a patient with a level of CYP2W1 higher than the predetermined value is likely to experience a more desirable clinical outcome than patients with levels of CYP2W1 lower than the predetermined value, or vice-versa. Levels of proteins and/or RNA, such as those disclosed in the present invention, are associated with clinical outcomes. One of skill in the art can determine such predetermined values by measuring levels of CYP2W1 in a patient population to provide a predetermined value. Optionally, a predetermined value for CYP2W1 level in one patient population can be compared to that from another to optimize the predetermined value to provide higher predictive value. In various embodiments, a predetermined value refers to value(s) that best separate patients into a group with more desirable clinical outcomes and a group with less desirable clinical outcomes. Such predetermined value(s) can be mathematically or statistically determined with methods well known in the art in view of this disclosure.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"QnD" or "qnd" refers to drug administration once every n days. For example, QD (or qd) refers to once every day or once daily dosing, Q2D (or q2d) refers to a dosing once every two days, Q7D refers to a dosing once every 7 days or once a week.

"Reduction" of a symptom or symptoms (and grammatical equivalents of this phrase) refers to decreasing the severity or frequency of the symptom(s), or elimination of the symptom(s).

"Solid tumor" refers to a cancer other than leukemia.

"Suitable for a therapy" or "suitably treated with a therapy" shall mean that the patient is likely to exhibit one or more desirable clinical outcome as compared to patients having the same cancer and receiving the same therapy but possessing a different characteristic that is under consideration for the purpose of the comparison. In one aspect, the characteristic under consideration is a genetic polymorphism or a somatic mutation. In another aspect, the characteristic under consideration is expression level of a gene or a polypeptide. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcome are considered simultaneously. In one such aspect, a patient possessing a characteristic, such as a genotype of a genetic polymorphism, may exhibit more than one more desirable clinical outcomes as compared to patients having the same cancer and receiving the same therapy but not possessing the characteristic. As defined herein, the patient is considered suitable for the therapy. In another such aspect, a patient possessing a characteristic may exhibit one or more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, progression free survival or overall survival is weighted more heavily than tumor response in a collective decision making.

"Therapeutically effective amount" of a drug refers to an amount of a drug that, when administered to a patient with cancer or other hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or other hyperproliferative disease; diminishment of extent of disease; delay or slowing of disease progression; amelioration, palliation, or stabilization of the disease state; or other beneficial results. Treatment of cancer may, in some cases, result in partial response or stable disease.

"Tumor" refers to an abnormal growth of tissue resulting from uncontrolled, progressive multiplication of cells and serving no physiological function. A tumor is also known as a neoplasm.

When a marker, such as CYP2W1, is "used as a basis" for identifying or selecting a patient for a treatment described herein, the marker can be measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of a biomarker in a clinical setting is a clear indication that this parameter was used as a basis for initiating, continuing, adjusting and/or ceasing administration of the treatments described herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Some abbreviations used in the description include:
CR—Complete Response
HAP(s)—Hypoxia Activated Prodrug(s)
mt—mutant
NSCLC—Non-Small Cell Lung Cancer
PD—Progressive disease
PDX tumor model—Patient-Derived tumor Xenograft model (grown subcutaneously in mice)
PR—Partial response
RECIST—Response Evaluation Criteria In Solid Tumors
TGI—Tumor growth inhibition
wt—wild-type Descriptive Embodiments The disclosure further provides diagnostic, predictive, prognostic and therapeutic methods, which are based, at least in part, on determination of the identity of the expression level of a marker of interest. In particular, the amount of CYP2W1 in a cancer patient sample can be used to predict whether the patient is likely to respond favorably to cancer therapy utilizing a hypoxia-activated prodrug of formula (I).

It shall also be understood that variants, mutants, parts or homologous protein sequences of CYP2W1 having the same function, are included in the scope of definition as well as protection. Possible alterations comprise deletion, insertion, substitution, modification and addition of at least one amino acid. Physiological fragments, secondary modifications, species-dependent alterations as well as allelic variants of CYP2W1 are also encompassed by the present invention. Preferably, the homology amounts to at least 85%, more preferably at least 95%, most preferably at least 98%. CYP2W1 may be named in different way but can be easily and uniquely assigned by the accession number (e.g., Q8TAV3), which is generally accepted and registered in data bases, such as UniProt.

Thus, information obtained using the diagnostic assays described herein is useful for determining if a subject is suitable for cancer treatment of a given type. Based on the predictive information obtained, a doctor can recommend a therapeutic protocol, which may include administration of a hypoxia-activated prodrug, useful for reducing the malignant mass or tumor in the patient or treat cancer in the individual.

In one aspect, a method is provided for treating cancer in a patient, comprising the steps of determining that a CYP2W1 RNA or protein level in a cancer sample isolated from said patient exceeds a predetermined level and administering to said patient a hypoxia-activated prodrug of formula (I)

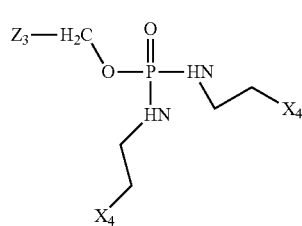

wherein $Z_3$ is selected from the group consisting of:

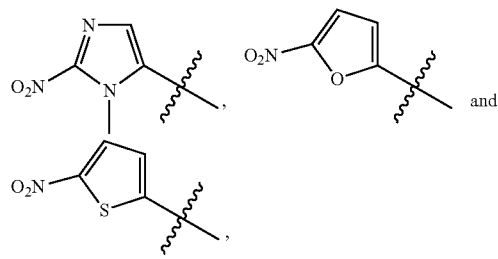

and $X_4$ is Cl or Br, or a physiologically acceptable salt thereof.

In another aspect, a method is provided for predicting the likelihood that a patient suffering from cancer, who is a candidate for treatment with a hypoxia-activated prodrug of formula (I), as defined above, will respond to the treatment with said prodrug, comprising the determination of the expression level of a prognostic gene or expression product thereof, which is CYP2W1, in a cancer sample obtained from said patient, wherein a higher expression indicates that the patient is likely to respond to said treatment compared to a predetermined value.

Still another aspect of the invention is a method, preferably an in-vitro method, for predicting the likelihood that a patient suffering from cancer will respond therapeutically to the treatment with a hypoxia-activated prodrug of formula (I), as defined above, comprising the steps of (i) measuring in a biopsy tissue sample from tumor tissue or plasma of said patient the expression level of CYP2W1 biomarker on protein basis, (ii) exposing said patient, preferably ex-vivo a tissue sample from tumor or plasma of said patient, to said prodrug, and (iii) measuring in said patient or exposed tissue sample of step (ii) the expression level of said biomarker specified in step (i) along with calculating the differences in expression levels measured in steps (i) and (iii), wherein a decrease in the expression level of said biomarker obtained in this step (iii) compared to step (i) indicates an increased likelihood that said patient will respond therapeutically to the treatment with said prodrug.

The reference value is defined by one or more of a specific functional or clinical property, and/or a specific, genetic or protein expression profile obtained from a reference patient or reference patient group. Said reference patient or patient group that does not express or express less gene product compared to the candidate patient. The reference value is an expression threshold value which is individually constituted or defined by specific clinical response parameters to be determined or by specific pre-treatment or treatment conditions. Suitable clinical response parameters are the progression free survival time (PFS), overall survival time (OS), partial response (PR), stable response (SR), progressive disease (PD) or combinations thereof.

For example, tissue or plasma samples are taken from the patient before treatment with the hypoxia-activated prodrug and optionally on treatment with the hypoxia-activated prodrug. The expression levels obtained on treatment are compared with the values obtained before starting treatment of said patient.

The information obtained may also be prognostic, in that it can indicate whether a patient has responded favorably or unfavorably to cancer therapy. Generally, if CYP2W1 levels rise after administration of a cancer therapy, the therapy may not be as efficacious as other therapies, and if CYP2W1 levels decline after therapy, the therapy is efficacious.

In one aspect, the invention also relates to a method for monitoring the likelihood of response to a treatment of cancer, which are mediated and/or propagated by hypoxia, wherein the CYP2W1 RNA or protein level is determined in a cancer sample withdrawn from a patient in need of such treatment with a hypoxia-activated prodrug of formula (I), as defined above, administered to said patient, wherein a decrease in CYP2W1 relative to a predetermined level of CYP2W1 in a cancer sample indicates an increased likelihood that said mammal responds to the treatment with said hypoxia-activated prodrug.

The identification of CYP2W1 provides a powerful tool for assessing the progression of a state, condition or treatment. The present invention can be used as a clinical marker to monitor efficacy of a compound of formula (I) on each patient individually. Specifically, CYP2W1 can be identified in a patient prior to an event, such as surgery, the onset of a therapeutic regime, or the completion of a therapeutic regime, to provide a base line result. This base-line can then be compared with the result obtained using identical methods either during or after such event. This information can be used for both diagnostic and prognostic purposes. The information about the clinical marker can be additionally used to optimize the dosage and the regimen of an active compound by monitoring the decrease of CYP2W1 in the subject's biological sample. Furthermore, the method of the present invention can be used to find a therapeutically effective compound and/or a therapeutically effective amount or regimen for the selected compound, thereby individually selecting and optimizing a therapy for a patient.

A patient's likely clinical outcome following a clinical procedure such as a therapy or surgery can be expressed in relative terms. For example, a patient having a particular CYP2W1 expression level who receives HAP therapy may experience relatively longer overall survival than a patient or patients not having the CYP2W1 expression level who receive HAP therapy. The patient having the particular CYP2W1 expression level, alternatively, can be considered as likely to survive if administered HAP therapy. Similarly, a patient having a particular expression level who receives HAP therapy may experience relatively longer progression free survival, or time to tumor progression, than a patient or patients not having the CYP2W1 expression level who receive HAP therapy. The patient having the particular CYP2W1 expression level, alternatively, can be considered as not likely to suffer tumor progression if administered HAP therapy. Further, a patient not having a particular CYP2W1 expression level who receives HAP therapy may experience relatively shorter time to tumor recurrence than a patient or patients having the expression level who receive HAP therapy. The patient having the particular CYP2W1 expression level, alternatively, can be considered as not likely to suffer tumor recurrence if administered HAP therapy. It is still another example that a patient having a particular expression level if administered HAP therapy may experience a relatively more complete response or partial response than a patient or patients not having the genotype or expression level who receive HAP therapy. The patient having the particular genotype or expression level, alternatively, can be considered as likely to respond to HAP therapy. Accordingly, a patient that is likely to survive, or not likely to suffer tumor progression, or not likely to suffer tumor recurrence, or likely to respond following a clinical procedure is considered suitable for the clinical procedure, treatment with a HAP.

It is to be understood that information obtained using the diagnostic assays described herein may be used alone or in combination with other information, such as, but not limited to, expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient, etc. When used in combination with other information, on the other hand, the information obtained using the diagnostic assays described herein is useful in aiding in the determination or identification of clinical outcome of a treatment, aiding in the selection of a patient for a treatment, or aiding in the treatment of a patient and the like. In a particular aspect, the expression level can be used in a diagnostic panel each of which contributes to the final diagnosis, prognosis, or treatment selected for a patient.

Thus, object of the invention is the use of CYP2W1 as biomarker for a hypoxia-activated prodrug of formula (I), as defined above and intended to be used for the treatment of cancer. The intended use is particularly a first-line treatment, and the prodrug is administered in mono-therapy. In an alternative embodiment of the intended use, said prodrug is combined with a chemotherapeutic agent, and said patient has developed chemo-refractory cancer.

The present invention arises out of the discovery that a cancer patient with high CYP2W1 level is more likely to respond favorably to HAP anti-cancer therapy than a cancer patient with a lower CYP2W1 level.

Diagnostic Methods

Thus, in one aspect, a method is provided for aiding in the selection of or selecting a hypoxia-activated prodrug therapy for a cancer patient, comprising, or alternatively consisting essentially of, or yet further consisting of, determining the CYP2W1 RNA or protein level in a sample isolated from the patient, wherein the hypoxia-activated prodrug therapy is selected for the patient if the level is equal to or exceeds a predetermined level (value) or the hypoxia-activated prodrug therapy is not selected if the level is below the predetermined level (value), wherein the hypoxia-activated prodrug therapy comprises, or alternatively consists essentially of, or yet further consists of a hypoxia-activated prodrug of formula (I)

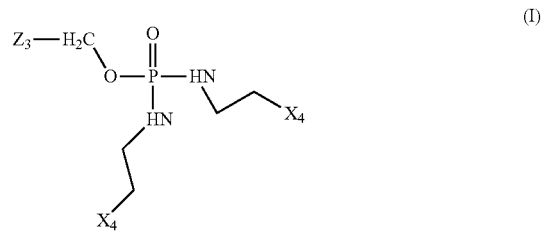

wherein $Z_3$ is selected from the group consisting of:

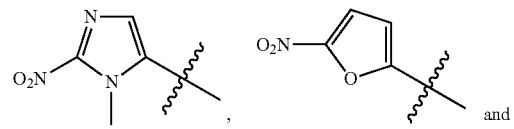
and

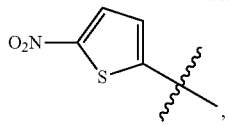

and $X_4$ is Cl or Br, or a physiologically acceptable salt thereof.

In one aspect, the CYP2W1 RNA level is determined relative to a control sample as Log 2 value with the predetermined value of 5.0 Log 2. In another aspect of the invention, the measured level exceeds the predetermined level in gall bladder PDX tumor model GL1208, or a non-small cell lung cancer PDX model selected from the group of LU1304, LU2505, LU1380, LU0357, LU1235 and LU0387. In one aspect, the therapy is selected for patients exhibiting progression-free survival as compared to similarly situated patients with the marker and did not receive the HAP therapy.

In one aspect, the hypoxia-activated prodrug therapy comprises, or alternatively consists essentially of, or yet further consists of (2-bromoethyl)({[(2-bromoethyl)amino][(2-nitro-3-methylimidazol-4-yl)methoxy]phosphoryl}) amine (TH-302) or (2-chloroethyl)({[(2-chloroethyl)amino][(2-nitro-3-methylimidazol-4-yl)methoxy]phosphoryl}) amine (TH-281).

In some embodiments, cancer patients that benefit from the diagnostic method include those suffering from various solid tumors, for example and without limitation, hypoxic solid tumors, blood cancers, and the like. In some embodiments, patients that benefit from the diagnostic method include those suffering from various solid tumors and undergoing monotherapy with TH-302. In a preferred embodiment of the invention, patients that benefit from the diagnostic method include those suffering from gall bladder cancer or non-small cell lung cancer.

Any suitable sample can be used for the method. Non-limiting examples of such include one or more of a serum sample, plasma sample, whole blood, pancreatic juice sample, tissue sample, tumor lysate or a tumor sample, which can be a isolated from a needle biopsy, core biopsy and needle aspirate.

Any suitable method can be used to measure the CYP2W1 protein, RNA, or other suitable read-outs for CYP2W1 levels, examples of which are described herein and/or are well known to the skilled artisan. In some embodiments, determining the level of CYP2W1 comprises determining the expression of CYP2W1, such as, e.g., by determining the CYP2W1 mRNA or CYP2W1 protein concentration in a patient sample. To this extent, mRNA of the sample can be isolated, if necessary, after adequate sample preparation steps, e.g. tissue homogenization, and hybridized with marker specific probes, in particular on a microarray platform with or without amplification, or primers for PCR-based detection methods, e.g. PCR extension labeling with probes specific for a portion of the marker mRNA.

In an embodiment of the invention, a DNA or RNA array comprises an arrangement of polynucleotides presented by or hybridizing to the CYP2W1 gene immobilized on a solid surface.

In further embodiments, the level of CYP2W1 is determined by the polypeptide or protein concentration of the CYP2W1, e.g., with CYP2W1 specific ligands, such as antibodies or specific binding partners. The binding event can, e.g., be detected by competitive or non-competitive methods, including the use of labeled ligand or CYP2W1 specific moieties, e.g., antibodies, or labeled competitive moieties, including a labeled CYP2W1 standard, which compete with marker proteins for the binding event. If the marker specific ligand is capable of forming a complex with the CYP2W1, the complex formation can indicate expression of the CYP2W1 in the sample.

Although the biomarker of the invention exhibits a sensitivity that allows its exclusive use in the scope of the methods described herein, it is another embodiment of the invention to apply more biomarkers in addition to the CYP2W1 marker. Analyzing multiple biomarkers increases screening stability and reduces error rates by covering a broader spectrum of responses than low-plurality reporter assays. In a preferred embodiment of the present invention, the expression levels of at least two, three, four, five, six, seven, eight, nine or ten biomarkers are determined, including CYP2W1. In a more preferred embodiment of the invention, CYP2W1 is determined in connection with a second biomarker. The particular combination of at least two biomarkers refines the correction with cancer susceptibility.

This disclosure also provides a kit for determining if a hypoxia-activated prodrug therapy is suitable for treatment of a cancer patient, comprising means for determining the serum protein level of a CYP2W1 protein, or the expression level of CYP2W1 RNA, in a sample isolated from the patient and instructions for use. In a further aspect, the kit further comprises the HAP therapy with a hypoxia-activated prodrug of formula (I). In one aspect of the invention, the determination of a high CYP2W1 level indicates increased PFS or OS when the patient is treated with said prodrug.

In one embodiment of the kit, the means for determining the CYP2W1 RNA level are nucleic acid probes that are capable of specifically hybridizing under stringent conditions with CYP2W1 or gene products encoded by said genes or respective parts thereof. In a preferred embodiment of the kit, a diagnostic kit for real-time PCR amplification of the CYP2W1 biomarker is provided, comprising a first package comprising the DNA or RNA of one or more of the CYP2W1, a second package comprising PCR primers which specifically hybridize with said DNA/RNA molecules of said first package, a third package comprising a well-plate or a respectively suitable container, and a fourth package comprising diagnostic means and solvents by means of which real-time PCR amplification can be carried out. In another embodiment of the kit, the means for determining the CYP2W1 protein level are antibodies with specific binding to CYP2W1.

Therapeutic Methods

Thus, in one aspect, the present invention provides a method for treating cancer in a patient comprising the steps of measuring CYP2W1 levels in a sample isolated from the patient, and administering a hypoxia-activated prodrug only if the CYP2W1 level measured is equal to or greater than a predetermined reference level, wherein the hypoxia-activated prodrug comprises, or alternatively consists essentially of, or yet further consists of a hypoxia-activated prodrug of formula (I)

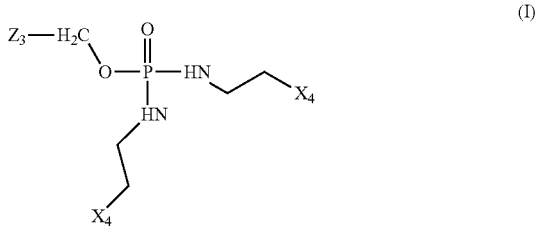

wherein $Z_3$ is selected from the group consisting of:

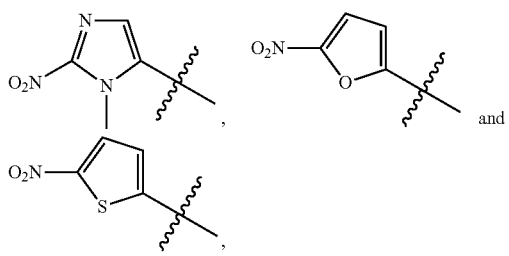

and $X_4$ is Cl or Br, or a physiologically acceptable salt thereof,
or administering a cancer therapy other than a therapy comprising administration of said hypoxia-activated prodrug of formula (I) if such measured level does not exceed said predetermined value.

In another aspect, the present invention provides a hypoxia-activated prodrug of formula (I) as defined above, for use in a method of treatment of cancer, optionally in combination with chemotherapy, in which the treatment is contra-indicated for cancer in which a CYP2W1 RNA or protein level is below a predetermined value or not present. In this context, the term "contra-indicated or "non-responsive", which are used interchangeably herein, means that a patient will not have a response according to RECIST criteria, or will have a reduced survival than a similar patient having high CYP2W1 level (see US 2009/0202989, incorporated herein by reference).

In still another aspect, the invention provides a method for advertising a hypoxia-activated prodrug of formula (I), as defined above, to a target audience, the use of said prodrug for treating a patient with cancer based on expression of CYP2W1 biomarker. Promotion may be conducted by any means available. In some embodiments, the promotion is by a package insert accompanying a commercial formulation of the hypoxia-activated prodrug of formula (I) (such as TH-302). The promotion may also be by a package insert accompanying a commercial formulation of a second medicament (when treatment is a combination therapy with a hypoxia-activated prodrug of formula (I) and a second medicament). Promotion may be by written or oral communication to a physician or health care provider. In some embodiments, the promotion is by a package insert where the package insert provides instructions to receive therapy with the hypoxia-activated prodrug of formula (I), and in some embodiments, in combination with a second medicament. In some embodiments, the promotion is followed by the treatment of the patient with the hypoxia-activated prodrug of formula (I) with or without the second medicament. In some embodiments, the promotion is followed by the treatment of the patient with the second medicament with or without treatment with the hypoxia-activated prodrug of formula (I). In some embodiments, the package insert indicates that the hypoxia-activated prodrug of formula (I) is to be used to treat the patient if the patient's cancer sample expressed high CYP2W1 biomarker. In some embodiments, the package insert indicates that the hypoxia-activated prodrug of formula (I) is not to be used to treat the patient if the patient's cancer sample expresses low CYP2W1 biomarker. In some embodiments, high CYP2W1 biomarker means likelihood of increased PFS and/or OS when the patient is treated with the hypoxia-activated prodrug of formula (I). In some embodiments, low CYP2W1 biomarker means likelihood of decreased PFS and OS when the patient is treated with the hypoxia-activated prodrug of formula (I). In some embodiments, the PFS and/or OS is decreased relative to a patient who is not treated with the hypoxia-activated prodrug of formula (I). In some embodiments, the promotion is by a package insert where the package inset provides instructions to receive therapy with TH-302. In some embodiments, the promotion is followed by the treatment of the patient with TH-302 with or without the second medicament. Further methods of advertising and instructing, or business methods are described in US 2012/0089541, which is incorporated herein by reference.

In one embodiment, the CYP2W1 level is measured based on the amount of CYP2W1 RNA in the sample. Preferably, the CYP2W1 RNA level is determined relative to a control sample, e.g. as Log 2 value. More preferably, the predetermined value is 5.0 Log 2. Using this value as the cut-off for dividing patients into high and low CYP2W1 level groups, one sees an even more dramatic example of the predictive value of CYP2W1 levels in determining whether a patient will respond to TH-302 or other HAP therapy with a compound of formula (I). It is surprisingly demonstrated that higher CYP2W1 levels correlated to a better response to TH-302 (see Table 1).

In another aspect of the invention, the measured level exceeds the predetermined level in gall bladder PDX tumor model GL1208, or a non-small cell lung cancer PDX model selected from the group of LU1304, LU2505, LU1380, LU0357, LU1235 and LU0387.

In one important embodiment, the HAP is (2-bromoethyl)({[(2-bromoethyl)amino][(2-nitro-3-methylimidazol-4-yl)methoxy]phosphoryl})amine (TH-302). In another embodiment, the hypoxia-activated prodrug comprises (2-chloroethyl)({[(2-chloroethyl)amino][(2-nitro-3-methylimidazol-4-yl)methoxy]phosphoryl})amine (TH-281). In one embodiment, the cancer patient is suffering from gall bladder cancer or NSCLC. In one embodiment, a patient sample is one or more of a plasma sample, serum sample, whole blood sample, pancreatic juice sample, tissue sample, tumor sample or tumor lysate.

In another embodiment, the hypoxia-activated prodrug is administered in an amount of 100 mg/m$^2$ to 700 mg/m$^2$ to the patient in need of cancer therapy. An individual patient's surface area can be determined using routine methods known to oncologists and other medical providers. For an adult human, a dose of 1 mg/m$^2$ of an active agent (drug) is equal to about 1.7 mg of that agent or drug per patient (i.e., the prototypical adult human has 1.7 m$^2$ of surface area). Therefore, for example, 100 mg/m$^2$ of a drug is equal to about 170 mg of that drug per patient. Further preferred dosage regimes in the meaning of the invention are disclosed in US 2013/0202716, which is incorporated herein by reference.

The hypoxia-activated prodrug can be adapted for administration via any desired suitable method, for example by oral (including buccal or sublingual), rectal, nasal, topical (including buccal, sublingual or transdermal), vaginal or parenteral (including intravenous, intraperitoneal, subcutaneous, intra-muscular or intradermal) methods. A preferred route of administration is a parenteral method, more preferably intravenous, intraperitoneal or subcutaneous injection.

In various embodiments, the CYP2W1 protein level is determined by a method comprising quantitative western blot, ELISA, immunohistochemistry, histochemistry, or use of FACS analysis of tumor lysates, immunofluorescence staining or Luminex technology. In another embodiment, the CYP2W1 RNA level is determined by a method comprising microarray chips, or RT-PCR, qRT-PCR, multiplex qPCR or in-situ hybridization.

Methods to Measure or Determine CYP2W1 Levels

CYP2W1 levels can be measured in accordance with the methods of the invention by any means known in the art. While CYP2W1 levels can be readily expressed in pg/mL from serum samples, other measurement units are readily useable in the methods of the invention by those of skill in the art upon contemplation of this disclosure.

In one embodiment, CYP2W1 levels are determined using an enzyme linked immunosorbent assay (ELISA). In one embodiment, CYP2W1 levels are determined using Western blot analysis. In one embodiment, CYP2W1 levels are determined using solid-phase extraction and matrix-assisted laser desorption/ionization mass spectrometry. In one embodiment, CYP2W1 levels are determined using surface-enhanced laser desorption/ionization time-of-flight (SELDI-TOF) mass spectrometry. In one embodiment, CYP2W1 levels are determined using protein arrays based on multiplexing a sandwich-ELISA system with chemiluminescent or fluorescent detection of analytes whose respective capture antibodies are spotted in arrays within each well of a sample plate (e.g., a 96-well microplate).

CYP2W1 levels from the tissue, serum or liquid sample to be analyzed may easily be detected or isolated using techniques which are well known to one of skill in the art, including but not limited to Western blot analysis. For a detailed explanation of methods for carrying out Western blot analysis, see, e.g., Sambrook and Russell (2001) "Molecular Cloning: A Laboratory Manual," Third Edition. The protein detection and isolation methods employed herein can also be such as those described in Harlow and Lane, (1999) "Using Antibodies: A Laboratory Manual." This can be accomplished, for example, by immunofluorescence techniques employing a fluorescently labeled antibody coupled with light microscopic, flow cytometric, or fluorimetric detection. The antibodies (or fragments thereof) useful in the present disclosure may, additionally, be employed histologically, as in immunofluorescence or immunoelectron microscopy, for in-situ detection of CYP2W1 levels. In-situ detection may be accomplished by removing a histological specimen from a patient, and applying thereto a labeled antibody. The antibody (or fragment) is preferably applied by overlaying the labeled antibody (or fragment) onto a biological sample. Through the use of such a procedure, it is possible to determine not only the presence of CYP2W1 levels, but also its distribution in the examined tissue. Using the present disclosure, one of ordinary skill will readily perceive that any of a wide variety of histological methods (such as staining procedures) can be modified in order to achieve such in situ detection.

The selected marker can be particularly used to establish screening tools with a higher throughput, such as Luminex xMAP technology. Luminex color-codes tiny beads, called microspheres, into 500 distinct sets. Each bead set can be coated with a reagent specific to a particular bioassay, allowing the capture and detection of specific analytes from a sample. The Luminex technology particularly combines a sandwich ELISA immobilized on microparticle beads and flow cytometry. It allows simultaneous quantitative measurement of several proteins in one single sample. Inside the Luminex analyzer, a light source excites the internal dyes that identify each microsphere particle, and also any reporter dye captured during the assay. Dual lasers are employed to detect identity of the beads (based on the spectral properties of the beads specific for each analyte) and the amount of associated Phycoerythrin (PE) fluorescence (Hoffmann et al, 2010, Toxicology 277, 49-58). Automated imaging platforms combining fluorescence microscopy with image analyses algorithms and informatics tools enable the analyses of fluorescent images from millions of cells with a high-resolution examination of the localization of cellular components, cellular macromolecular structures and the temporal dynamics of cellular functions.

Many different types of assays are known, examples of which are set forth below, including analyses by nucleotide arrays and nucleotide filters. The hybridization conditions (temperature, time, and concentrations) are adjusted according to procedures also well known in the art. It is preferred to apply chip hybridization and/or PCR for the determination of gene expression. In another preferred embodiment, the assay of the invention involves the use of a high density oligonucleotide array. In still another preferred embodiment, the analysis is performed by multiplex qPCR, more preferably low density TaqMan arrays or branched DNA assays. Other solid supports and microarrays are known and commercially available to the skilled artisan.

The measurement of levels of expression may be carried out using any techniques that are capable of measuring RNA transcripts in a biological sample. Examples of these techniques include, without being limited thereto, PCR, Northern blotting, TaqMan, Primer Extension, Differential display and nucleotide arrays, among other things.

In another embodiment, the total RNA from the patient sample is prepared by methods known to the skilled artisan such as by Trizol (Invitrogen) followed by subsequent re-purification, e.g. via Rneasy columns (Qiagen). The total RNA is used to generate a labeled target according to methods and using detectable labels well-known in the art. For instance, the RNA may be labeled with biotin to form a cRNA target for use in an assay. Next, with the extracted mRNA as a template, cDNAs are produced using a reverse transcriptase (for example, SuperScript Reverse Transcriptase; GibcoBRL) and labeled dNTP (for example, Cy3-dUTP and Cy5-dUTP; Amersham Pharmacia Biotech), and a cDNA sample that reflects the amount of genes expressed within the cells to be evaluated is prepared. This causes labeled cDNA to be included in the cDNA sample. Here, either fluorescent label or radiolabel may be used as a label. The cDNA sample prepared in this manner is applied to the below-mentioned microarray in its single stranded denatured form, and cDNAs included in the cDNA sample are hybridized with the genes immobilized on the basal plate.

According to a preferred embodiment of the invention, the Polymerase Chain Reaction or PCR is an amplification-based assay used to measure the copy number of the gene. Detailed protocols for real-time quantitative PCR are known in the art, for example, for RNA.

Methods of real-time quantitative PCR using TaqMan probes are well-known in the art. Hence, a TaqMan-based assay can be applied to quantify polynucleotides. TaqMan based assays use a fluorogenic oligonucleotide probe that contains a 5'-fluorescent dye and a 3'-quenching agent. The probe hybridizes to a PCR product, but cannot itself be extended due to a blocking agent at the 3'-end. When the PCR product is amplified in subsequent cycles, the 5'-nuclease activity of the polymerase, for example, AmpliTaq, results in the cleavage of the TaqMan probe. This cleavage separates the 5'-fluorescent dye and the 3'-quenching agent, thereby resulting in an increase in fluorescence as a function of amplification.

The analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion. Optical images viewed and optionally recorded by a camera or other recording device (e.g. a photodiode and data storage device) are optionally further processed in any of the embodiments herein, e.g. by digitizing the image, storing and/or analyzing the image on a computer. A variety of commercially available peripheral equipment and software is available for digitizing, storing and analyzing a digitized video or digitized optical image. One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g. by fluorescent or dark field microscopic techniques.

Further methods are disclosed in US 2009/0202989, US 2010/0221754, US 2011/0275088, US 2012/0089541 and US 2013/0102493, each of which is incorporated herein by reference in its entirety.

Thus, any of a variety of means can be used to assess CYP2W1 levels in a patient or sample taken from the patient for the purpose of predicting whether the patient will respond favorably to hypoxia-activated prodrug therapy. If the CYP2W1 level in the patient or patient sample is higher than or equal to a predetermined value for the CYP2W1 level, the patient is administered a HAP therapy, such as TH-302, but if the CYP2W1 level is below that predetermined value, then the patient is administered an anti-cancer therapy other than HAP therapy.

EXAMPLE

Most solid tumors have significant areas of hypoxia that contain cells that are resistant to traditional chemotherapy and radiation treatment. Thus, therapeutics that can specifically target these resistant hypoxic zones should provide additional anti-tumor activity and clinical benefit. TH-302 is a hypoxia-targeted prodrug of a DNA alkylating agent that is being tested in multiple oncology clinical trials. More specifically, TH-302 is a nitroimidazole-linked prodrug of a brominated version of isophosphoramide mustard (Br-IPM). When exposed to hypoxic conditions, TH-302 is reduced at the nitroimadazole site of the prodrug by intracellular reductases leading to the release of Br-IPM. Br-IPM can then act as a DNA crosslinking agent. There are several factors that affect the sensitivity of different cancer models to TH-302 including the degree of hypoxia in the tumor, intracellular reductase enzymes such as NADPH:cytochrome P450 (CYPOR) and mutations in DNA repair genes such as BRCA1, BRCA2 or FANCA. The precise one-electron reductase enzymes in different cancer cell types that can mediate the activation of TH-302 under hypoxic conditions are currently not well understood.

In previous tumor xenograft studies from a variety of different tumor types, the monotherapy efficacy of TH-302 was modest since tumor growth delays were typically observed in a panel of 11 cancer cell-line derived models (Sun et al., 2012, Clin Cancer Res 18:758-770). This level of efficacy is consistent with a mechanism of action of TH-302 whereby TH-302 targets the hypoxic tumor regions that typically comprise 2-20% of the entire tumor.

A series of tumor xenograft experiments was initiated. In these gall bladder and NSCLC tumor experiments, patient-derived tumor xenograft (PDX) models were selected since these models more accurately mimic the histology and genetics of actual human tumors as compared with the cell line derived models. More specifically, the original tumor sources for these human tumor xenograft models were patient-derived (PDX) gall bladder and lung carcinomas that have been maintained subcutaneously in nude mice for >3 passages. When grown to 500-700 mm$^3$, the tumors were harvested for inoculation by selecting and slicing (into 3×3×3 mm$^3$ fragments) well grown portions of tumors. These tumor fragments were implanted subcutaneously in the right flank of athymic nu/nu mice (female, 6-8 weeks old (18-20 g)) for the efficacy experiments. All of the procedures for tumor harvesting, inoculation, animal dosing, and tumor and body weight measurement were conducted in a sterile hoods.

For the efficacy studies, when the average tumor size reached 100-200 mm$^3$, mice were randomly grouped into vehicle and TH-302 treatment groups. Each group contained 8-10 mice. Since the tumor volume could affect the effectiveness of any given treatment, a randomized block design was used in the group assignment based upon their tumor volumes. This ensured that all the groups were comparable at the baseline. After randomization, mice were treated with either vehicle or TH-302 i.p. 60 mg/kg twice per week (Q2W) for approximately 5-8 weeks based on tumor grow rate and response. The precise dosing periods are described in the legends of FIGS. 1 and 2 above. Tumor volumes were measured twice weekly.

%ΔT/ΔC was calculated with the formula below:

$$\%\Delta T/\Delta C = ((TV_f - TV_i)/(TV_{fCtrl} - TV_{iCtrl})) \times 100\%$$

where TV=tumor volume, f=final, I=initial, and Ctrl=control group.

If tumor regression was observed:

$$\%\Delta T/\Delta C = (TV_f - TV_i)/TV_i \times 100\% = \% \text{ Regression} = (1 - (TV_f/TV_i)) \times 100\%$$

where TV=tumor volume, f=final, I=initial, and Ctrl=control group.

Tumor response criteria: %ΔT/ΔC>20%: tumor growth inhibition; %ΔT/ΔC between −30% to ≤20%: tumor stasis/tumor regression; %ΔT/ΔC<−30%: tumor regression; Non-palpable tumors: complete regression.

Figure 1B:
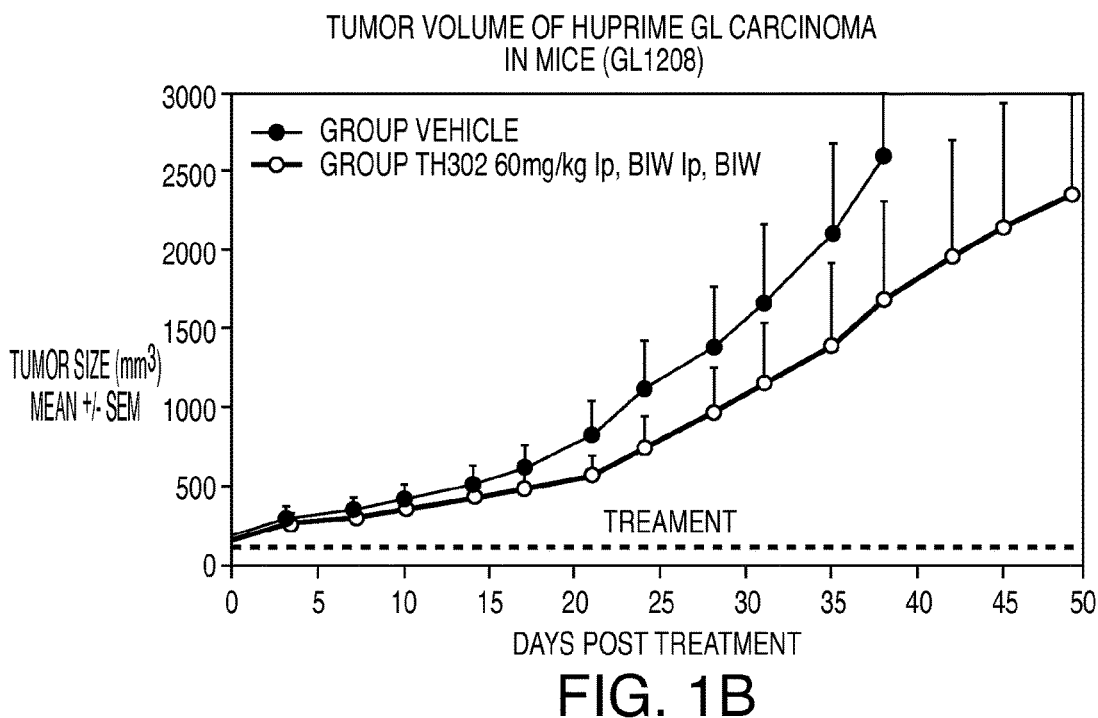
Figure 2A:
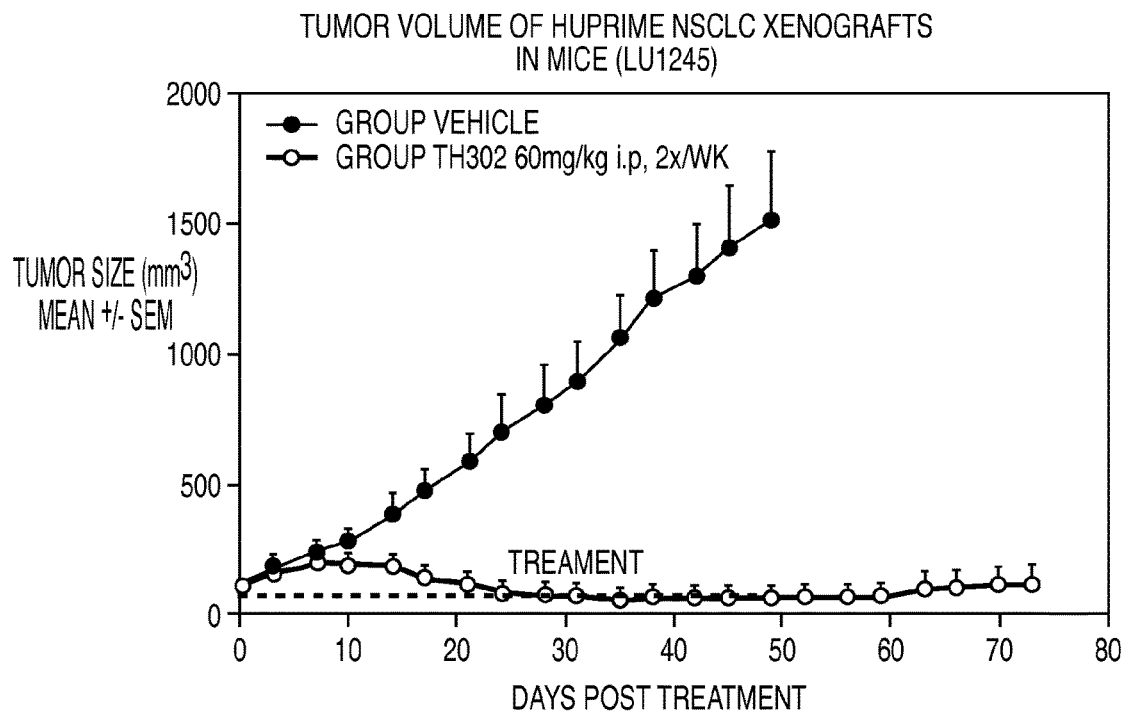
FIG. 2 shows the antitumor activity of TH-302 in 2 human non-small cell lung cancer PDX xenograft models (LU1245 and LU1380). TH-302 was administered at 60 mg/kg i.p. on a twice per week (Q2W) dosing schedule and tumor growth measurements were plotted. A: The LU1245 NSCLC PDX xenograft model was highly sensitive to TH-302 with clear tumor regressions observed with a 49 day dosing period. 5/10 mice had a complete response as defined by the lack of tumor re-growth following regression at day 73 (14 days post treatment termination). B: The LU1380 NSCLC PDX xenograft model showed minor tumor growth inhibition (TGI) after 42 days treatment. This minor level of efficacy in LU1380 was similar to that observed in 5 other NSCLC xenograft models shown in table 1 (LU1304, LU2505, LU0357, LU1235, LU0387). No significant changes in the body weights of the mice treated with TH-302 were observed in these studies (data not shown).
Figure 2B:
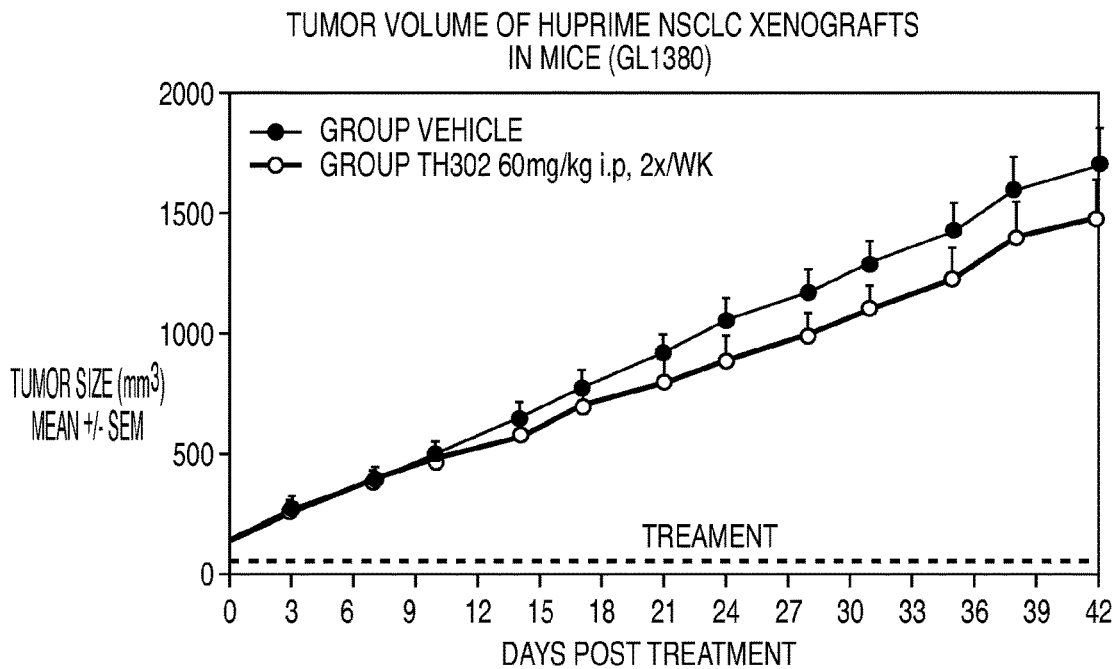
Figure 3:
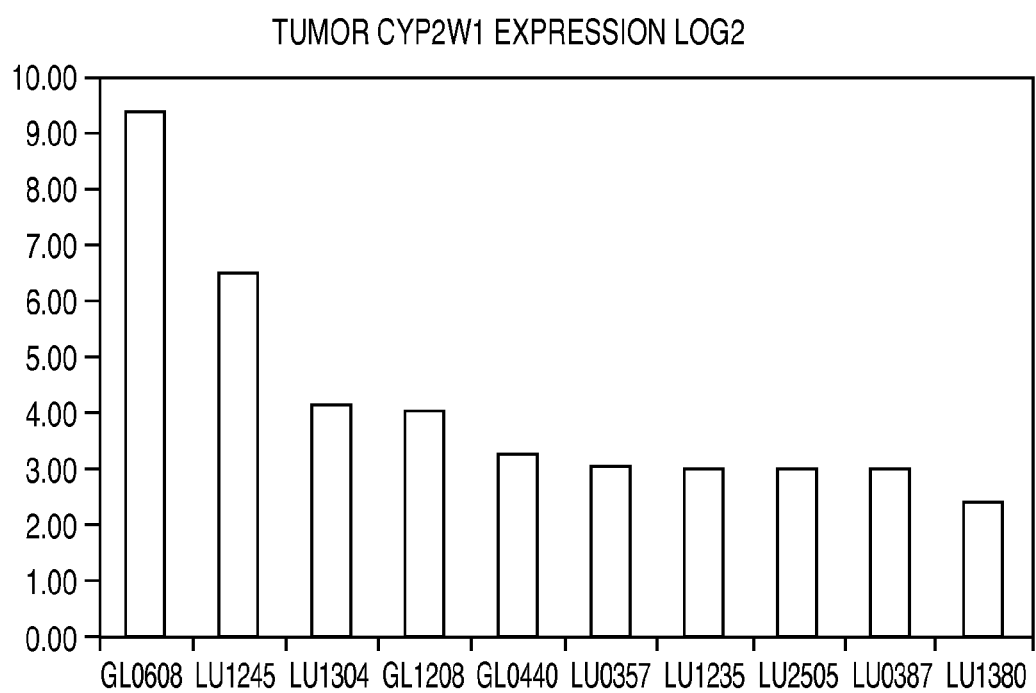
FIG. 3 shows RNA expression level of CYP2W1 (probe set 11737840_x_at) across a panel of 10 PDX models that were used in this analysis. CYP2W1 RNA expression data were obtained from the Crown Bioscience HuBase database. The PDX tumor models showing high sensitivity to TH-302 with tumor regressions and complete responses (GL0608 and LU1245) are shown along with the weakly sensitive models (GL1208, LU1304, LU2505, LU0357, LU1235, LU0387). The expression level of CYP2W1 is the highest in GL0608 among 4 gall bladder cancer models available at Crown Biosciences and highest in LU1245 among 50 NSCLC cancer models available at Crown Biosciences; 7 of which were tested in efficacy studies (see Table 1).

Surprisingly, in 2 gall bladder models and 7 NSCLC models tested, 1 gall bladder model (GL0608) and 1 NSCLC model (LU1245) were highly sensitive to TH-302 with tumor regression and complete responses observed in the mice (FIGS. 1, 2).

Figure 4:
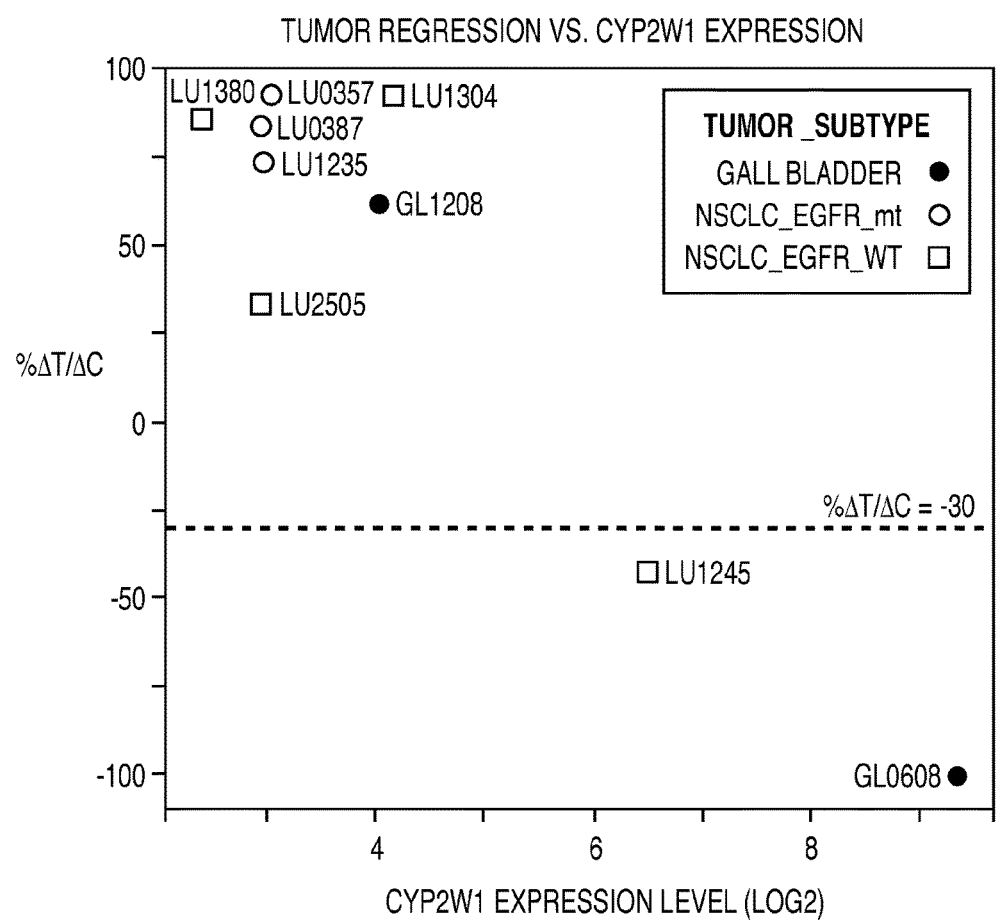
FIG. 4 shows a plot of TH-302 efficacy (%ΔT/ΔC) vs. CYP2W1 RNA expression levels in 9 PDX xenograft models (2 gall bladder, 4 NSCLC EGFR wt, 3 NSCLC EGFR mt). The dashed line shows the %ΔT/ΔC cutoff (~30%) that identifies models with clear tumor regression. GL1208 and GL0608 refer to gall bladder tumor subtype. LU0357, LU0387 and LU1235 refer to NSCLC_EGFR_mt. LU1380, LU1304, LU2505 and LU1245 refer to NSCLC_EGFR_wt.

Analysis of the gene expression microarray profiling data (Affymetrix HG_U219 data) from three gall bladder models (GL0608, GL1208 and GL440) was performed. These microarray data were normalized using the robust multi-array average (RMA) method (Irizarry et al., 2003, Biostatistics 4: 249-264). The genes were then ranked according to their differential expression between GL0608 and GL1208. Expression values were reported as log 2 values. The cut-off was defined such that genes were overexpressed by at least 5.0 Log 2 (or 32-fold relative overexpression). Among these genes, CYP2W1 (probe set 11737840_x_at) was identified as a candidate biomarker. CYP2W1 was overexpressed 43.4 fold in GL0608 compared to GL1208. The expression levels of CYP2W1 in the lung cancer models tested and in NSCLC models available at Crown Biosciences were further investigated. The expression level of CYP2W1 in the lung cancer model LU1245, where tumor regressions and CRs were observed, was the highest among 50 PDX NSCLC models and among the 7 NSCLC models tested (Table 1, FIG. 4).

TABLE 1

Summary of TH-302 efficacy (%ΔT/ΔC) and CYP2W1 RNA expression levels in 10 PDX xenograft models (3 gall bladder cancer, 4 NSCLC EGFR wt, 3 NSCLC EGFR mt). Gene expression profiling data (Affymetrix HG_U219) were available for all 10 models and efficacy data were available for all models except GL0440. Gene expression profiling data for GL0440 were used to normalize the gall bladder microarray data by the robust multi-array average (RMA) method. A high level of efficacy in GL0608 and LU1245 is shown by these %ΔT/ΔC-data and the tumor regressions and CRs (FIGS. 1, 2). High levels of CYP2W1 RNA expression were also observed in the GL0608 and LU1245 models compared with the other models.

| Tumor type | PDX tumor model name | Tumor model description (age/sex, pathology) | %ΔT/ΔC (TH-302) | CYP2W1 RNA expression level (probe set 11737840_x_at) |
|---|---|---|---|---|
| Gall Bladder | GL0608 | 73/F, adenocarcinoma | −100% | 9.34 |
| Gall Bladder | GL1208 | unknown, adenosquamous | 62% | 4.03 |
| Gall Bladder | GL0440 | 59/F, adenocarcinoma | n.d. | 3.28 |
| NSCLC, EGFR wt | LU1245 | 57/M, adenocarcinoma | −42% | 6.50 |
| NSCLC, EGFR wt | LU1304 | 75/F, adenocarcinoma | 93% | 4.16 |
| NSCLC, EGFR wt | LU2505 | 69/M, adenocarcinoma | 34% | 2.95 |
| NSCLC, EGFR wt | LU1380 | 75/M, adenocarcinoma | 86% | 2.40 |
| NSCLC, EGFR mt | LU0357 | 60/F, squamous | 93% | 3.04 |
| NSCLC, EGFR mt | LU1235 | 56/F, adenosquamous | 74% | 2.98 |
| NSCLC, EGFR mt | LU0387 | 64/F, adenocarcinoma | 84% | 2.94 |

Taken together, these data and analyses identified CYP2W1 as a potential enzyme involved in the reduction and activation of TH-302 in tumors, and they identified CYP2W1 expression levels as a potential biomarker to predict which patients will be most likely to show a high level of response to TH-302.

The invention claimed is:

1. A method for treating cancer overexpressing CYP2W1 RNA or protein in a patient, comprising the steps of determining that a CYP2W1 RNA or protein level in a cancer sample isolated from said patient exceeds a predetermined level and administering to said patient a hypoxia-activated prodrug, wherein the hypoxia-activated prodrug comprises (2-bromoethyl)({[(2-bromoethyl)amino][(2-nitro-3-methyl-imidazol-4-yl)methoxy]phosphoryl})amine (TH-302) and wherein the cancer patient is suffering from gall bladder cancer or non-small cell lung cancer.

2. The method according to claim 1, wherein the CYP2W1 RNA level is determined relative to a control sample as Log 2 value with the predetermined value of 5.0 Log 2.

3. The method according to claim 1, wherein CYP2W1 RNA or protein measured level exceeds the predetermined level in gall bladder PDX tumor model GL1208, or a non-small cell lung cancer PDX model selected from the group of LU1304, LU2505, LU1380, LU0357, LU1235 and LU0387.

4. The method of claim 1, wherein the hypoxia-activated prodrug is administered in an amount of 100 mg/m$^2$ to 700 mg/m$^2$ to the patient in need of cancer therapy.

5. The method of claim 1, wherein the patient sample is one or more of a serum sample, plasma sample, whole blood sample, pancreatic juice sample, tissue sample, tumor sample or tumor lysate.

6. The method of claim 1, wherein the CYP2W1 RNA level is determined by a method comprising PCR, qRT-PCR, multiplex qPCR or in-situ hybridization, or the CYP2W1 protein level is determined by a method comprising immunohistochemistry, histochemistry, western blot, FACS, immunofluorescence staining or Luminex technology.

* * * * *